Feb. 7, 1967 H. C. SWIM ETAL Plant Pat. 2,709
ROSE PLANT
Filed Nov. 22, 1965
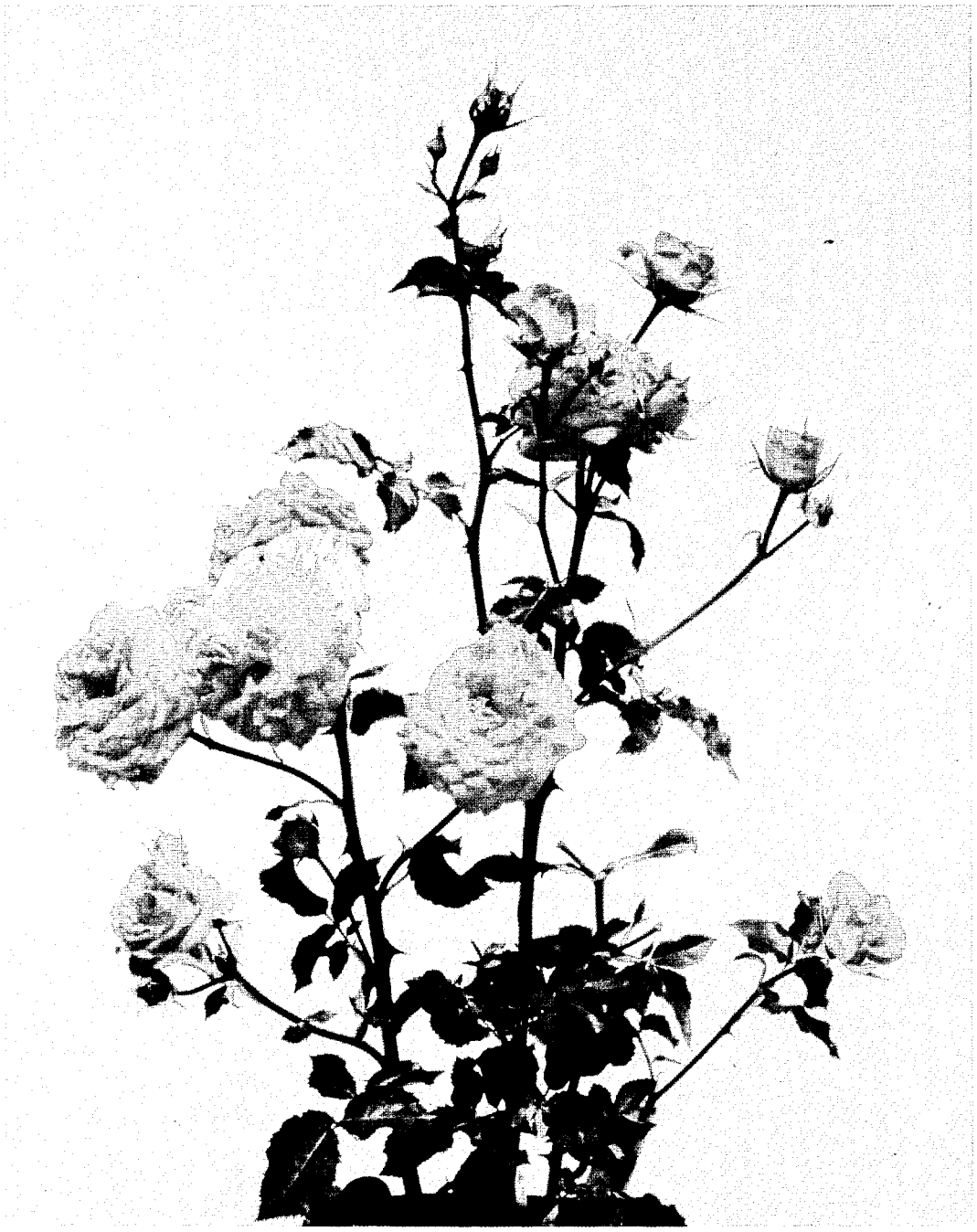
Inventors.
H. C. Swim
O. L. Weeks
By: Robb & Robb
Attorneys.

United States Patent Office

Plant Pat. 2,709
Patented Feb. 7, 1967

2,709
ROSE PLANT

Herbert C. Swim, Ontario, and O. L. Weeks, Chino, Calif., assignors to O. L. Weeks, doing business as Weeks Wholesale Rose Grower, Chino, Calif.

Filed Nov. 22, 1965, Ser. No. 509,228
1 Claim. (Cl. Plt.—25)

The present invention relates to a new and distinct variety of rose plant of the polyantha class, which was originated by us by crossing an unnamed and unpatented seedling of "Circus" (Plant Patent No. 1,382) × "Garnette (unpatented) with the variety known as "Spartan" (Plant Patent No. 1,357).

As the result of this breeding, we have produced a new and improved rose variety having the following unique combination of characteristics which are outstanding therein and which distinguish it from its parents, as well as from all other varieties of which we are aware:

(1) A dwarf and compact habit of growth which makes the plant suitable for use in low hedges or borders;

(2) A short pointed form of the flower buds;

(3) A relatively small flower size, with accompanying more or less continuous flower production;

(4) Heavy petalage of the individual flowers;

(5) An unusually long lasting quality of the flowers both on the plant and when cut;

(6) A habit of cleaning off the old flowers, as well as the peduncles, shortly after the flowers have changed color and as they begin to wither; and (7) A distinctive, attractive, and bright Strong Reddish-Orange general color tonality of the flowers, with relative uniformity of the flower color throughout the life of each individual flower.

In comparison with its unnamed seed parent, the new variety has a relatively smaller plant size and is more compact; the flower stems are substantially shorter and heavier; the flower bud form is short-pointed instead of long-pointed to urn-shaped like the parent; the flowers have substantially greater petalage ranging from 75 to 80 petals per flower instead of only 25 to 28 as in the flowers of this parent; the substance and lasting quality of the flowers are substantially greater; and instead of bi-colored but generally bright red flowers like the parent, the flower color of the new variety does not show any substantial degree of difference between the inner and reverse surfaces of the petals and the color may be generally described as bright orange in the newly opened flower.

As compared with its pollen parent "Spartan," the plant of the new variety is moderately dwarf instead of moderately tall; the flowers are smaller in size but have substantially greater petalage; and the flowers have substantially longer lasting quality both on the bush and when cut, with attendant heavier substance.

A sexual reproduction of our new variety by budding, as performed at Chino, California, shows that the aforementioned characteristics and distinctions come true to form and are established and transmitted through succeeding propagations.

The accompanying drawing shows typical specimens of the vegetative growth and flowers of our new variety in different stages of development and as depicted in color as nearly true as it is reasonably possible to make the same in a color illustration of this character.

The following is a detailed description of our new variety, with color terminology in accordance with the Nickerson Color Fan, published by Munsell Color Company, Incorporateed, of Baltimore, Maryland, except where general color terms of ordinary dictionary significance are obvious:

Type: Dwarf; bush; outdoor; seedling; for garden decoration.

Class: Polyantha.

Breeding: Seedling.

*Seed parent.*—An unnamed seedling of "Circus" × "Garnette."

*Pollen parent.*—"Spartan."

Propagation: Holds its distinguishing characteristics through succeeding propagations by budding.

*Flower*

Locality where grown and observed: Ontario, California.

Flowers borne: From singly to several to stem; in irregular and somewhat flat clusters; on strong, short stems.

Quantity of bloom: Free, outdoors.

Continuity: More or less continuous.

Fragrance: From none to slight.

Bud:

*Peduncle.*—Short; heavy caliper; erect and stiff on primary flowers, but often bending on secondary flowers; smooth except for few stipitate glands. Color—reddish on exposed side and green on protected side.

*Before calyx breaks.*—Size—from medium to small. Form—short; oval; with a conspicuous neck; with foliaceous appendages on the surface of the bud; sometimes with foliaceous parts extending beyond the tip of the bud equal to ¼ to ½ or more of its length. Color—Vivid Red, Plate 5R 5/13.

*As calyx breaks.*—Color—from Vivid Red, Plate 5R 5/13 to Strong Reddish-Orange, Plate 7.5R 5/13.

*As first petal opens.*—Size—small. Form—short; from flat to pointed. Color: outside—point of attachment surrounded by small area of greenish-white, with remainder of petal near Vivid Red, Plate 5R 5/13; inside—point of attachment surrounded by small area of greenish-white which sometimes extends in broad vegetative pattern toward apex along general area of midrib, with remainder of petal near Strong Reddish-Orange, Plate 7.5R 5/13.

*Opening.*—Opens up well.

Bloom:

*Size (when fully open).*—From small to medium for class; from 2 inches to 2¼ inches.

*Petalage.*—Double; usually with no stamens showing; from 75 to 80 petals; arranged more or less regularly.

*Form.*—Flat at first, but becoming flat to slightly high-centered; petals being at first flat, but later becoming loosely rolled outward at maturity.

Petals:

*Texture.*—Thick; leathery.

*Appearance.*—Inside—satiny; outside—shiny.

*Shape.*—Outside—somewhat broader than long, with apex acute. Intermediate—ovate, with apex acute. Inside—ovate, with apex rounded.

This description of a newly opened flower was made from a rose grown outdoors during the month of October at Ontario, California:

*Color.*—Outer petal: outside surface—prominent area at base greenish-white, with remainder Deep Yellowish-Pink, Plate 5R 6/11; inside surface—prominent area at base greenish-white, with remainder near Strong Reddish-Orange, Plate 7.5R 5/13. Intermediate petal: outside surface—small area at base greenish-white, with remainder between Deep Pink, Plate 2.5R 6/11 and Deep Yellowish-Pink, Plate 5R 6/11; inside surface—greenish-white immediately about point of attachment, with remainder near Strong Reddish-Orange, Plate 7.5R 5/13. Inner petal: outside surface—greenish-white at point of attachment, with some tendency to striated extensions of this color, and with remainder of petal between Deep Pink, Plate 2.5R 6/11 and Strong Red, Plate 2.5R 5/12; inside surface—small area about point of attachment yellowish-white, with remainder between Vivid Red, Plate 5R 5/13 and Strong Reddish-Orange, Plate 7.5R 5/13.

This description was made from a rose that was open for three days outdoors during the month of October at Ontario, California:

*Color.*—Outer petal: outside surface—relatively large area at base near white, with remainder of petal between Strong Yellowish-Pink, Plate 5R 7/9 and Deep Yellowish-Pink, Plate 5R 6/11; inside surface—prominent area at base near white, with remainder of petal between Strong Reddish-Orange, Plate 7.5R 6/12 and Deep Yellowish-Pink, Plate 5R 6/11, except at extreme margin which is nearer Strong Reddish-Orange, Plate 7.5R 5/13. Inner petal: outside surface—prominent area at base near white, with remainder of petal between Deep Pink, Plate 2.5R 6/11 and Deep Yellowish-Pink, Plate 5R 6/11; inside surface—prominent area at base near white, with remainder near Strong Reddish-Orange, Plate 7.5R 6/12, except for such portion of apex exposed to light which is between Vivid Red, Plate 5R 5/13 and Strong Reddish-Orange, Plate 7.5R 5/13.

*General color effect.*—Newly opened flower—strong Reddish-Orange, Plate 7.5R 5/13. 3-days open—Strong Reddish-Orange, Plate 7.5R 5/13, especially at tips where exposure to light is greatest, but where exposure is small or recent, color is nearer Reddish-Orange, Plate 7.5R 6/12.

*Behavior.*—Drop off cleanly with peduncle after flower has withered slightly; persist until flower has withered slightly and color has changed to a pinkish-red.

*Flower longevity.*—On bush in garden—9 days in October. Cut roses grown outdoors and kept at living-room temperatures—7 days in October.

*Reproductive organs*

Stamens: Many; arranged more or less regularly about pistils; some mixed with petaloids.
Filaments: Short; most with anthers. Color—from greenish-white to greenish-yellow.
Anthers: From small to medium size; open at various times. Color—yellow, with reddish reverse markings.
Pollen: Color—gold.
Pistils: Medium in quantity.
Styles: Uneven; short; variable caliper; loosely bunched.
Stigma: Color—white, with reddish-purple margin.
Ovaries: Most protruding from calyx.
Hips: None observed; rarely set naturally.
Sepals: Falling soon with peduncle; moderately short; fairly straight; recurved.
Seeds: None observed.

*Plant*

Foliage:

*Leaves.*—Compound of 3 to 7 leaflets; moderately sparse; from small to medium size; heavy; leathery; glossy.

*Leaflets.*—Shape—ovate-lanceolate, with holly-like laterals. Apex—acute, with acuminate terminals. Base—round on terminals and somewhat cuneate on laterals. Margin—simply serrate.

*Color.*—Mature: upper surface—dark green, with reddish-purple margins; under surface—grey-green, with reddish-purple margins. Young: upper surface—shiny light yellowish-green, with reddish-purple margins; under surface—light green, with reddish-purple overlay especially at margins and on serrations.

*Rachis (the supporting stem of the compound leaf).*—Medium weight. Upper side—grooved; few stipitate glands. Under side—sparsely prickly; some few scattered stipitate glands.

*Stipules.*—From short to medium length; medium width; with short to medium length points turning out at an angle of 45°.

*Disease resistance.*—Good resistance to powdery mildew as determined by comparison with a wide variety of rose varieties grown in the nursery row under comparable cultural conditions at Ontario, California.

Growth:

*Habit.*—Dwarf; bushy; upright-spreading; much-branched.

*Growth.*—Moderately free, but low.

*Canes.*—Moderately heavy caliper for length.

*Main stems.*—Color—dull olive green. Large prickles—several; medium length; straight; with narrow base of medium length; color—grey-brown. Small prickles—few; color—grey-brown. Hairs—none.

*Branches.*—Color—bright green. Large prickles—several; medium length; straight; with narrow base of medium length; color—brown. Small prickles—few; color—brown. Hairs—none.

New shoots.—Color—bright green, with reddish-purple margins. Large prickles—several; from short to medium length; straight; with short, narrow base; color—reddish-purple. Small prickles—few; color—reddish-purple. Hairs—none.

We claim:

A new and distinct variety of rose plant of the polyantha class, substantially as herein shown and described, characterized particularly as to novelty by the unique combination of a dwarf and compart habit of growth which makes the plant suitable for use in low hedges or borders, a short pointed form of the flower buds, a relatively small flower size, with accompanying more or less continuous flower production, heavy petalage of the individual flowers, an unusually long lasting quality of the flowers both on the plant and when cut, a habit of cleaning off the old flowers, as well as the peduncles, shortly after the flowers have changed color and as they begin to wither, and a distinctive, attractive, and bright Strong Reddish-Orange general color tonality of the flowers, with relative uniformity of the flower color throughout the life of each individual flower.

No references cited.

ABRAHAM G. STONE, *Primary Examiner.*

R. E. BAGWILL, *Examiner.*